United States Patent [19]

Karube et al.

[11] Patent Number: 5,580,762
[45] Date of Patent: Dec. 3, 1996

[54] METHOD OF PRODUCING AN OLIGOSACCHARIDE OF A HIGHER POLYMERIZATION DEGREE

[75] Inventors: Isao Karube, Kawasaki; Takashi Morita, Tokyo, both of Japan

[73] Assignee: Akebono Brake Industry Co. Ltd., Tokyo, Japan

[21] Appl. No.: 211,919

[22] PCT Filed: Aug. 25, 1993

[86] PCT No.: PCT/JP93/01192

§ 371 Date: Jun. 20, 1994

§ 102(e) Date: Jun. 20, 1994

[30]  Foreign Application Priority Data

Aug. 25, 1992 [JP] Japan ................................ 4-226155
Aug. 6, 1993 [JP] Japan ................................ 5-196373

[51] Int. Cl.$^6$ .......................... C12P 19/14; C12P 19/04; C12P 19/20; C12P 19/22
[52] U.S. Cl. .................. 435/99; 435/95; 435/96; 435/98; 435/101
[58] Field of Search .................. 435/95, 99, 101, 435/96, 98

[56]  References Cited

U.S. PATENT DOCUMENTS 3,692,580  9/1972  Hirao et al. ........................ 127/29
4,604,352  8/1986  Zeikus et al. ........................ 435/42
4,717,662  1/1988  Montgomery ........................ 435/99

OTHER PUBLICATIONS

Publication No. 63-196297 (A); Aug. 15, 1988; JP; Appl. No. 62-27471; Feb. 9, 1987; "Production of Maltooligosaccharide Derivative".

Publication No. 4-210597 (A); Jul. 31, 1992; JP; Appl. No.2-410180; Dec. 12, 1990; "Production of Starchy Saccharide Containing Maltohexaose and Maltoheptaose".

Publication No. 4-66094 (A); Mar. 2, 1992; JP; Appl.No. 2-176917; Jul. 4, 1990; "Enzymatic Decomposition of Starch-Containing Material and Production of Oligosaccharide".

Primary Examiner—John W. Rollins
Assistant Examiner—Francisco C. Prats
Attorney, Agent, or Firm—Knobbe Martens Olson & Bear

[57]  ABSTRACT

The present invention is a method of producing an oligosaccharide of a higher polymerization degree by enzymatic hydrolyzing of a polysaccharide with a hydrolase capable of cleaving the bonds among sugars constituting the polysaccharide comprising step of making the polysaccharide coexist with the hydrolase in a mixture of water and a hydrophilic organic solvent such as ethanol.

6 Claims, 9 Drawing Sheets

METHOD OF PRODUCING AN OLIGOSACCHARIDE OF A HIGHER POLYMERIZATION DEGREE

TECHNICAL FIELD

The present invention relates to a method of producing an oligosaccharide of a higher polymerization degree. More specifically, the present invention relates to a method of producing an oligosaccharide of a higher polymerization degree by using as a raw material polysaccharide.

BACKGROUND ART

Because it has been known recently that sugars are involved in physiological functions, the studies on sugars are actively promoted. Also, oligosaccharides having a variety of activities have been known, including those of lower cariosity, those having a function capable of normalizing enterobacteria, those having bacteriostatic action, or those having inclusion activity such as cyclodextrin. Such oligosaccharides have made contributions to food industry and the like.

Although some oligosaccharides are directly produced as fermentation products, a great number of oligosaccharides are generally produced through polysaccharide degradation. Conventional process of degrading polysaccharide has been performed enzymatically in aqueous medium or with acid hydrolysis.

However, a great number of the oligosaccharides produced by enzymatic degradation in aqueous media are of lower molecules of nearly dimer to hexamer, particularly dimer or trimer. The yield of an oligosaccharide of a higher polymerization degree than those described above especially 10 or more is low, so the production thereof at a higher efficiency is generally hard.

Oligosaccharides of a lower polymerization degree are for use in low-calory sweeteners or sweeteners of low cariosity. Alternatively, it is said that those of a higher polymerization degree may have a function to increase useful enterobacteria such as *Lactobacillus bifidus* and the like. However, because oligosaccharides of a higher polymerization degree are produced with difficulty, their studies have not made any advance. Therefore, oligosaccharides of a higher polymerization degree or the process of producing the same have been expected strongly.

In starch industry, pullulanase is used in combination with a variety of amylases so as to improve the yield of glucose and maltose. However, it has never been known the use of pullulanase for the generation of an oligosaccharide of a higher polymerization degree.

From the respect described above, the present invention has been carried out for the object to produce an oligosaccharide of a higher polymerization degree at a higher efficiency and to provide a method of producing an oligosaccharide of a higher polymerization degree through enzymatic degradation, by using polysaccharide as a raw material.

DISCLOSURE OF THE INVENTION

The present inventors have made intensive investigations so as to achieve the objective described above, and have then found that an oligosaccharide of a higher polymerization degree is produced by using a hydrophilic organic solvent in a reaction system for enzymatic degradation. Thus, the inventors have achieved the invention.

That is, the present invention is a method of producing an oligosaccharide of a higher polymerization degree by degrading polysaccharide with a hydrolase capable of cleaving the bonds among sugars constituting the polysaccharide comprising step of making the polysaccharide coexist with the hydrolase in a mixture of a hydrophilic organic solvent and water.

In accordance with the present invention, the term "oligosaccharide of a higher polymerization degree" means primarily the one of nearly pentamer to 20-mer.

The present invention will now be explained in details.

As has been described above, a method of producing an oligosaccharide of a higher polymerization degree in accordance with the present invention comprises effecting enzymatic degradation in a mixture of a hydrophilic organic solvent and water, by using polysaccharide as a raw material.

The polysaccharide as a raw material includes for example starch, cellulose, chitin, chitosan, dextran, agar, xylan and the like.

An enzyme capable of cleaving the bonds among sugars constituting the polysaccharide is used as the enzyme for the enzymatic degradation, and for the polysaccharide described above, use is made of for example amylase, pullulanase, cellulase, chitinase, chitosanase, dextranase, agarase, and xylanase, respectively. These enzymes are classified in endo-type capable of random cleavage of the inside of the polysaccharide and exo-type capable of terminal cleavage. Endo-type is preferable in accordance with the present invention. Also, if it is preferable that a generated oligosaccharide does not have any side chain, the branched bonds should preliminarily be cleaved with an enzyme for cleaving branched chains, such as isoamylase.

The enzymatic reaction may be effected in liquid phase, but the reaction may be effected by using an enzyme immobilized on an insoluble carrier, ie. so-called immobilized enzyme. In accordance with the present invention, any immobilization method may be used.

The hydrophilic organic solvent to be used in the enzymatic reaction includes, for example, polar non-proton solvents such as acetone, dioxane, tetrahydrofurane, acetonitrile, dimethyl sulfoxide, dimethyl formamide and the like, in addition to alcohols as polar proton solvents, such as ethanol, methanol, propanol, butanol, pentanol, hexanol and the like. The enzymatic reaction is carried out in a mixture system of these hydrophilic organic solvents and water. When starch is degraded with α-amylase, ethanol is particularly preferable; and the concentration of ethanol is preferably 30 to 90 v/v %. In terms of yield, furthermore, when ethanol concentration is higher, starch concentration is preferably 20 w/v % or less in the reaction solution.

The hydrolase, the hydrophilic organic solvent and its concentration for use may appropriately be determined, depending on the polysaccharide to be used as the raw material and the polymerization degree of the oligosaccharide to be generated. For instance when starch is used as the polysaccharide, amylase and ethanol may be illustrated as the hydrolase and the hydrophilic organic solvent, respectively. In this case when ethanol concentration is then elevated, an oligosaccharide of a higher polymerization degree can be obtained, whereas the total yield tends to be lowered. When pullulanase is used as a hydrolase together with amylase, however, an oligosaccharide of a higher polymerization degree can be generated at a higher yield.

The enzymatic reaction is preferably carried out under the conditions optimum to the enzyme to be used, but the reaction may also be carried out satisfactorily under mild conditions so as to increase the polymerization degree of the generated oligosaccharide. For example, the condition at 50° C. and pH 6.0 to 7.0 is optimum for degrading starch with α-amylase.

The polymerization degree of an oligosaccharide to be generated should be adjusted by modifying the reaction conditions, specifically the reaction time, the enzyme level to the raw material substrate, etc. The conditions may satisfactorily be predetermined by the HPLC (high-performance liquid chromatography) or any other analysis of the reaction products.

So as to obtain an oligosaccharide of a desirable polymerization degree from the reaction products, the oligosaccharide should be separated by gel filtration or HPLC. For the reaction system with ethanol concentration of 60 v/v % or more, most of the oligosaccharide of a higher polymerization degree is generated as precipitate. Then, the precipitate is gathered by centrifuging. Furthermore, the precipitate in separation is dissolved at an appropriate concentration, and is then purified by gel filtration etc., if necessary.

For example, α-amylase is a hydrolase of endo-type capable of randomly cleaving the α-1,4 glucoside bond of starch. However, if the water concentration is lowered in the reaction system, the equilibrium of the reaction is modified toward conversion or synthesis in the reverse direction. That is, by effecting such enzymatic reaction in a hydrophilic organic solvent of a higher concentration, the reaction equilibrium is sifted to generate an oligosaccharide of a higher polymerization degree, which cannot be generated in an aqueous system. It is through such action that the present invention is applicable when a polysaccharide other than starch is employed along with an enzyme hydrolyzing the polysaccharide.

In accordance with the present invention, no potential contamination of bacteria can be introduced because the reaction is effected in an organic solvent, so that no sterilization procedure or equipment therefor can be required.

BEST MODE OF CARRYING OUT THE INVENTION

The examples of the present invention will now be described hereinbelow in details, illustrating a method of producing gluco-oligosaccharide from starch. Herein, the immobilized enzyme to be used in Example 2 and thereafter was prepared as follows; an excess amount of an enzyme solution (undiluted solution) was added to CHITOPEARL BCW-3510 (manufactured by Fuji Boseki, Co., Ltd.) of a wet wight of 10 g in 30 ml of a buffer, followed by gradual stirring at room temperature for 1 hour, which was then left to stand overnight or longer at 4° C. for the immobilization of the enzyme. The solution of the immobilized enzyme was used at 0.6 to 1.0 g (by wet weight) in 10 ml of the reaction solution. In any case, the enzyme reaction was effected by standing alone the reaction mixture.

The ethanol concentration hereinbelow described was represented by v/v % in a mixture of 50 mM phosphate buffer.

The reaction products were analyzed by HPLC, after the enzyme was inactivated by 10-min heating at 90° C. after the reaction. The ratios of the individual oligosaccharides of various polymerization degrees to the total weights of the resulting reaction products (excluding unreacted substrate) were calculated.

For HPLC analysis, use was made of LC-6AD and RID-6A, manufactured by SHIMADZU, CO. LTD.; for the column, TSKgel AMIDE80 or Asahipak NK2P-50 was used.

Example 1

Explanation will firstly be done about an example with use of a non-immobilized enzyme.

Wheat starch was suspended at 10 w/v % in 0, 30, 40, 50, and 60% ethanol solution (pH 7.0), followed by addition of 100 μl of 0.24 KNU (kilonovo unit; 1 KNU corresponds to an enzyme amount capable of degrading 5.25 g starch per hour) α-amylase (BAN240L derived from *Bacillus subtilis*; commercially available from NOVO INDUSTRY)) for reaction at 50° C. for 96 hours.

Figure 1:
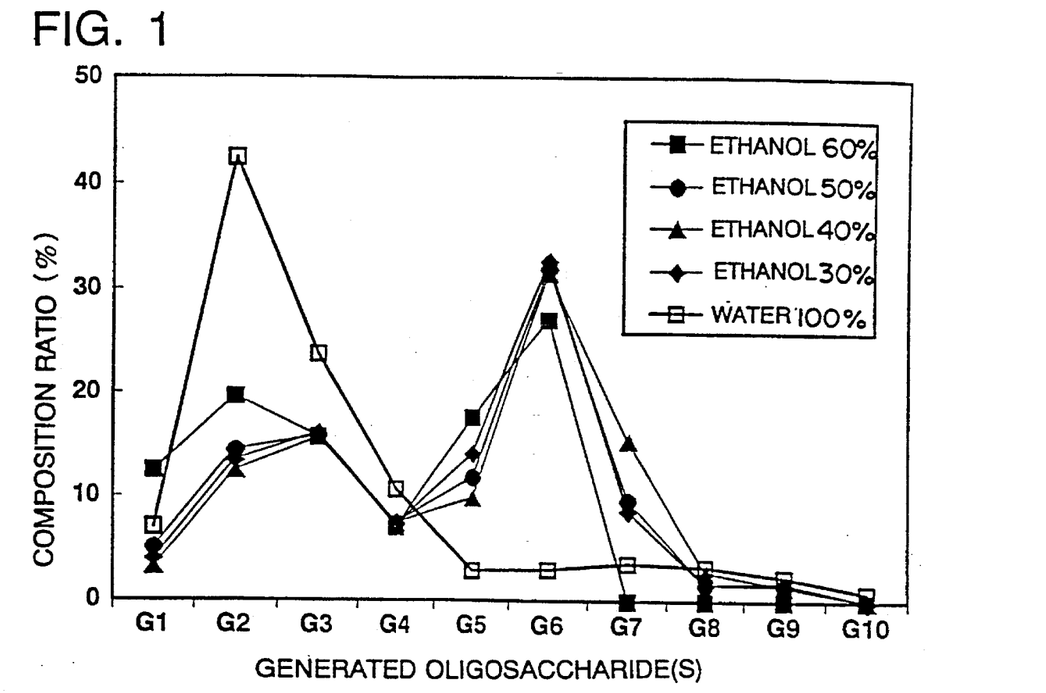
FIG. 1 is a set of graphs depicting the ratios of individual oligosaccharides of various polymerization degrees to the total amount of the reaction products.

After the reaction, the concentrations of the oligosaccharides contained in the supernatants were measured. The ratios of the individual oligosaccharides of various polymerization degree to the total amount are shown in Table 1 and FIG. 1.

TABLE 1

| Polymerization degree | Ethanol concentration (v/v %) | | | | |
|---|---|---|---|---|---|
| | 0 | 30 | 40 | 50 | 60 |
| 1 | 7.1 | 4.1 | 3.3 | 5.2 | 12.5 |
| 2 | 42.5 | 13.5 | 12.5 | 14.5 | 19.7 |
| 3 | 23.8 | 16.2 | 15.7 | 15.9 | 15.8 |
| 4 | 10.7 | 7.3 | 7.5 | 7.5 | 7.1 |
| 5 | 2.9 | 14.2 | 9.9 | 11.9 | 17.7 |
| 6 | 3.0 | 32.8 | 31.6 | 32.1 | 27.1 |
| 7 | 3.6 | 8.7 | 15.4 | 9.7 | 0 |
| 8 | 3.3 | 1.6 | 2.8 | 1.6 | 0 |
| 9 | 2.3 | 1.7 | 1.4 | 1.5 | 0 |

TABLE 1-continued

| Polymerization | Ethanol concentration (v/v %) | | | | |
|---|---|---|---|---|---|
| degree | 0 | 30 | 40 | 50 | 60 |
| 10 | 0.8 | 0 | 0 | 0 | 0 |
| Yield (%) (in supernatant) | 55.8 | 28.1 | 18.2 | 15.4 | 1.7 |

From these results, it is indicated that the addition of ethanol to the reaction system increased the ratios of the oligosaccharides of pentamer or more, compared with the ratios of those in the system with water alone. Furthermore, the increase of ethanol concentration markedly decreased the total weights (yield) of the oligosaccharides relative to the weight of the raw material, which was due to the fact that the elevation of the polymerization degree precipitated the resulting products in ethanol as indicated by subsequent experiments.

Example 2

Explanation will be done about an example using an immobilized enzyme.

Figure 2:
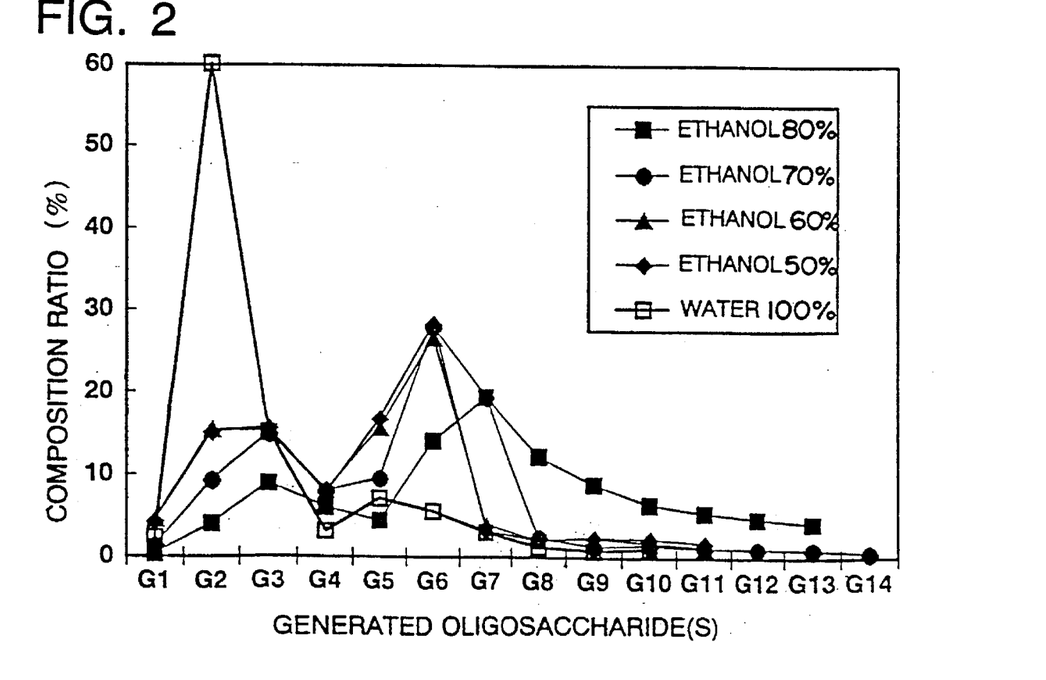
FIG. 2 is a set of graphs depicting the ratios of individual oligosaccharides of various polymerization degrees to the total amount of the reaction products.

Using the immobilized BAN240L in 30 ml of the buffer, 10 w/v % wheat starch solution was degraded as in Example 1 (reaction time; 120 hours). For the analysis of the reaction products, the supernatant after the reaction was analyzed in case of water alone; the precipitate in the reaction solution was dissolved in hot water and then subjected to the analysis in case of 60, 70 and 80% ethanol; both of the supernatant and the precipitate were subjected to the analysis in case of 50% ethanol. The results are shown in Table 2 and FIG. 2.

TABLE 2

| Polymerization | Ethanol concentration (v/v %) | | | | |
|---|---|---|---|---|---|
| degree | 0 | 50 | 60 | 70 | 80 |
| 1 | 2.4 | 4.4 | 4.6 | 1.4 | 0.4 |
| 2 | 60.2 | 15.1 | 15.4 | 9.3 | 4.1 |
| 3 | 15.1 | 15.7 | 15.3 | 15.0 | 9.0 |
| 4 | 3.2 | 7.8 | 8.2 | 8.1 | 6.1 |
| 5 | 7.2 | 16.8 | 15.7 | 9.6 | 4.5 |
| 6 | 5.6 | 28.4 | 26.7 | 28.0 | 14.1 |
| 7 | 3.1 | 3.3 | 4.1 | 19.5 | 19.5 |
| 8 | 1.3 | 2.1 | 2.1 | 2.5 | 12.3 |
| 9 | 0.8 | 2.4 | 2.4 | 1.3 | 8.9 |
| 10 | 1.1 | 2.3 | 1.8 | 1.5 | 6.5 |
| 11 | 0 | 1.8 | 1.3 | 1.2 | 5.5 |
| 12 | 0 | 0 | 0 | 1.1 | 4.8 |
| 13 | 0 | 0 | 0 | 1.0 | 4.2 |
| 14 | 0 | 0 | 0 | 0.6 | 0 |
| Yield (%) precipitate | 0 | 32.5 | 56.9 | 100 | 50.6 |
| Yield (%) supernatant | 12.0 | 55.8 | 0 | 0 | 0 |

These results indicate that the oligosaccharides of higher polymerization degrees in the reaction products were greater in ratio and yield in higher concentrations of ethanol.

Example 3

Figure 3:
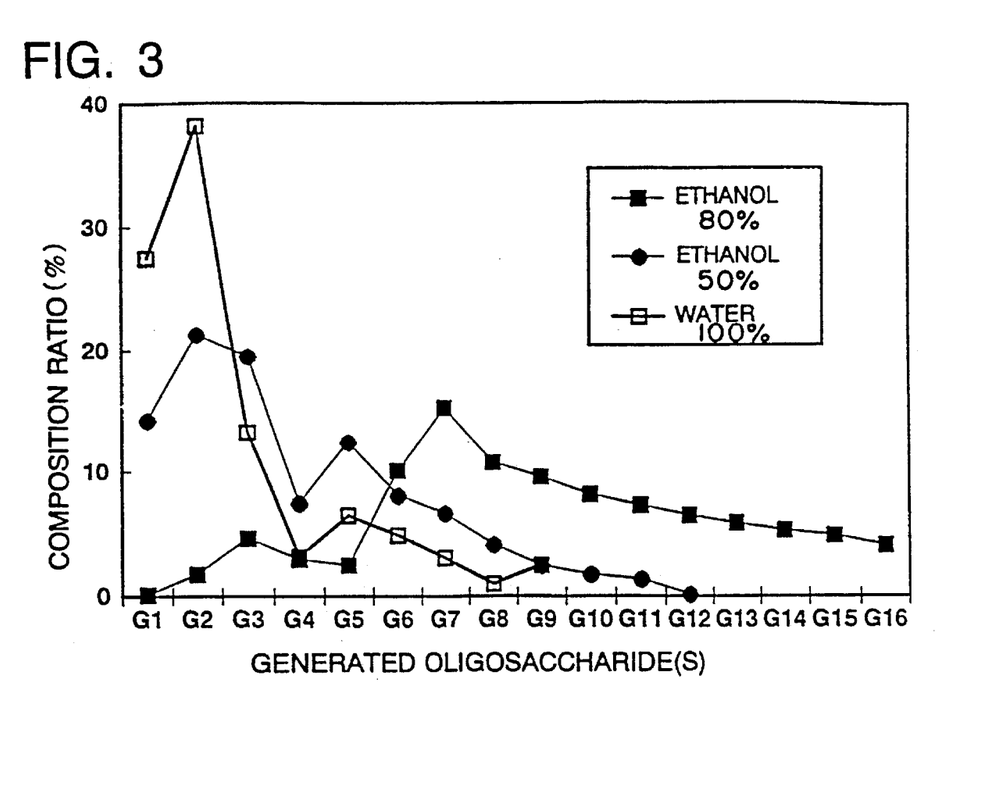
FIG. 3 is a set of graphs depicting the ratios of individual oligosaccharides of various polymerization degrees to the total amount of the reaction products.

Using 0.8 g of the immobilized α-amylase derived from Bacillus subtilis (manufactured by Wako Junyaku Kogyo, Co. Ltd.; Type 015-03731 for chemical experiments) in 10 ml of the reaction solution, the reaction was done (for 70 hours) as in Example 2. The products whose polymerization degrees were 1 to 16 were subjected to analysis. The results are shown in Table 3 and FIG. 3.

TABLE 3

| polymerization | ethanol concentration (V/V %) | | |
|---|---|---|---|
| degree | 0 | 50 | 80 |
| 1 | 27.5 | 14.3 | 0.14 |
| 2 | 38.2 | 21.4 | 1.8 |
| 3 | 13.3 | 19.6 | 4.7 |
| 4 | 3.2 | 7.5 | 3.0 |
| 5 | 6.5 | 12.5 | 2.5 |
| 6 | 4.9 | 8.1 | 10.1 |
| 7 | 3.1 | 6.7 | 15.3 |
| 8 | 1.0 | 4.2 | 10.8 |
| 9 | 2.5 | 2.5 | 9.6 |
| 10 | 0 | 1.8 | 8.2 |
| 11 | 0 | 1.4 | 7.3 |
| 12 | 0 | 0.2 | 6.5 |
| 13 | 0 | 0 | 5.9 |
| 14 | 0 | 0 | 5.3 |
| 15 | 0 | 0 | 4.9 |
| 16 | 0 | 0 | 4.1 |
| Yield (%) precipitate | 0 | 69.7 | 29.8 |
| Yield (%) supernatant | 12.6 | — | 0 |

As apparently shown in these results, oligosaccharides of higher polymerization degree degrees were generated as the precipitate in the reaction solution, following the increase in the ethanol concentration.

Example 4

Using next different immobilized enzymes, degradation products were compared.

Figure 4A:
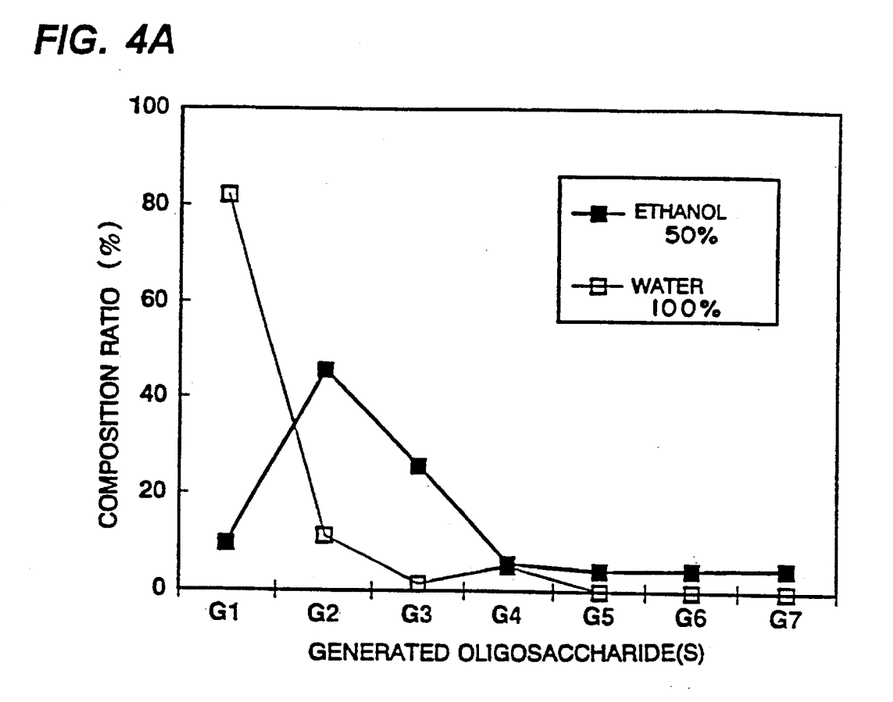
FIG. 4 is sets of graphs depicting the ratios of individual oligosaccharides of various polymerization degrees to the total amount of the reaction products.
Figure 4B:
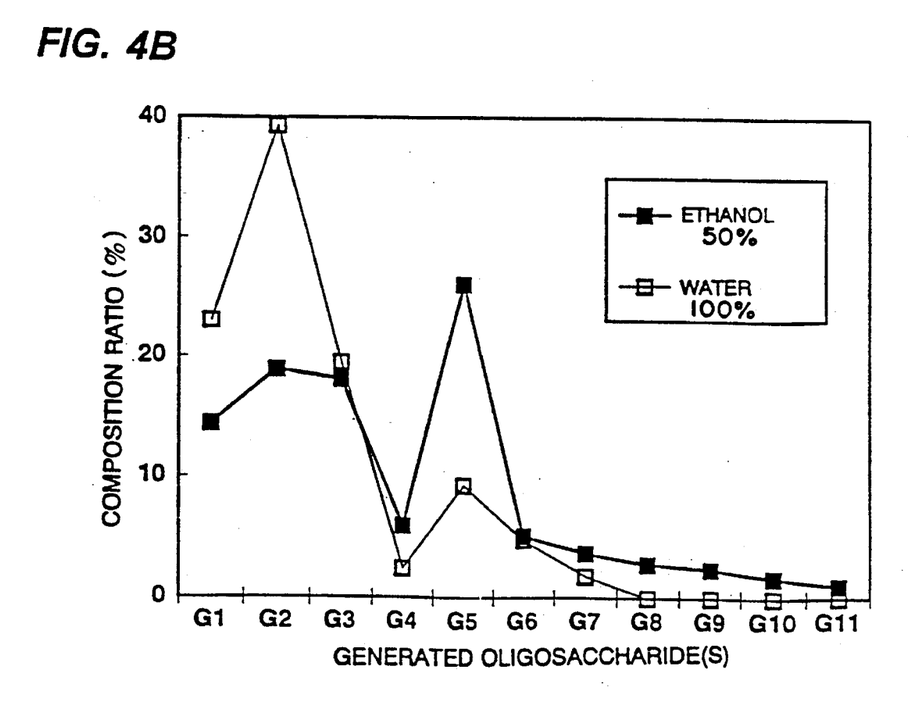

Using 0.8 g each of α-amylase derived from Aspergillus orizae (NOVO INDUSTRY, CO. LTD.; Fungamil 800L) and α-amylase derived from Bacillus licheniformis (NOVO INDUSTRY, CO. LTD.; Termamil 120L,) in 10 ml of the reaction solution, enzymatic degradation was carried out (for 70 hours) as in the above Example). Then, the reaction products in the supernatant and precipitate were subjected to analysis. The results are shown in Table 4 and FIG. 4 (A; Fungamil, B; Termamil).

TABLE 4

| polymar-ization | Fungamil 800L | | Termamil 120L | |
|---|---|---|---|---|
| degree | ethanol 0% | ethanol 50% | ethanol 0% | ethanol 50% |
| 1 | 82.1 | 9.7 | 23.0 | 14.4 |
| 2 | 11.3 | 45.7 | 39.3 | 18.9 |
| 3 | 1.5 | 25.8 | 19.5 | 18.1 |
| 4 | 5.1 | 5.6 | 2.4 | 5.9 |
| 5 | 0 | 4.2 | 9.2 | 26.1 |
| 6 | 0 | 4.4 | 4.8 | 5.1 |
| 7 | 0 | 4.7 | 1.8 | 3.7 |
| 8 | 0 | 0 | 0 | 2.8 |
| 9 | 0 | 0 | 0 | 2.4 |
| 10 | 0 | 0 | 0 | 1.7 |
| 11 | 0 | 0 | 0 | 1.0 |
| Yield (%) | 3.0 | 8.2 | 22.2 | 88.6 |

Consequently, oligosaccharides of higher polymerization degrees were generated when ethanol was added to the reaction solution even if any of the enzymes was employed.

Example 5

Figure 5:
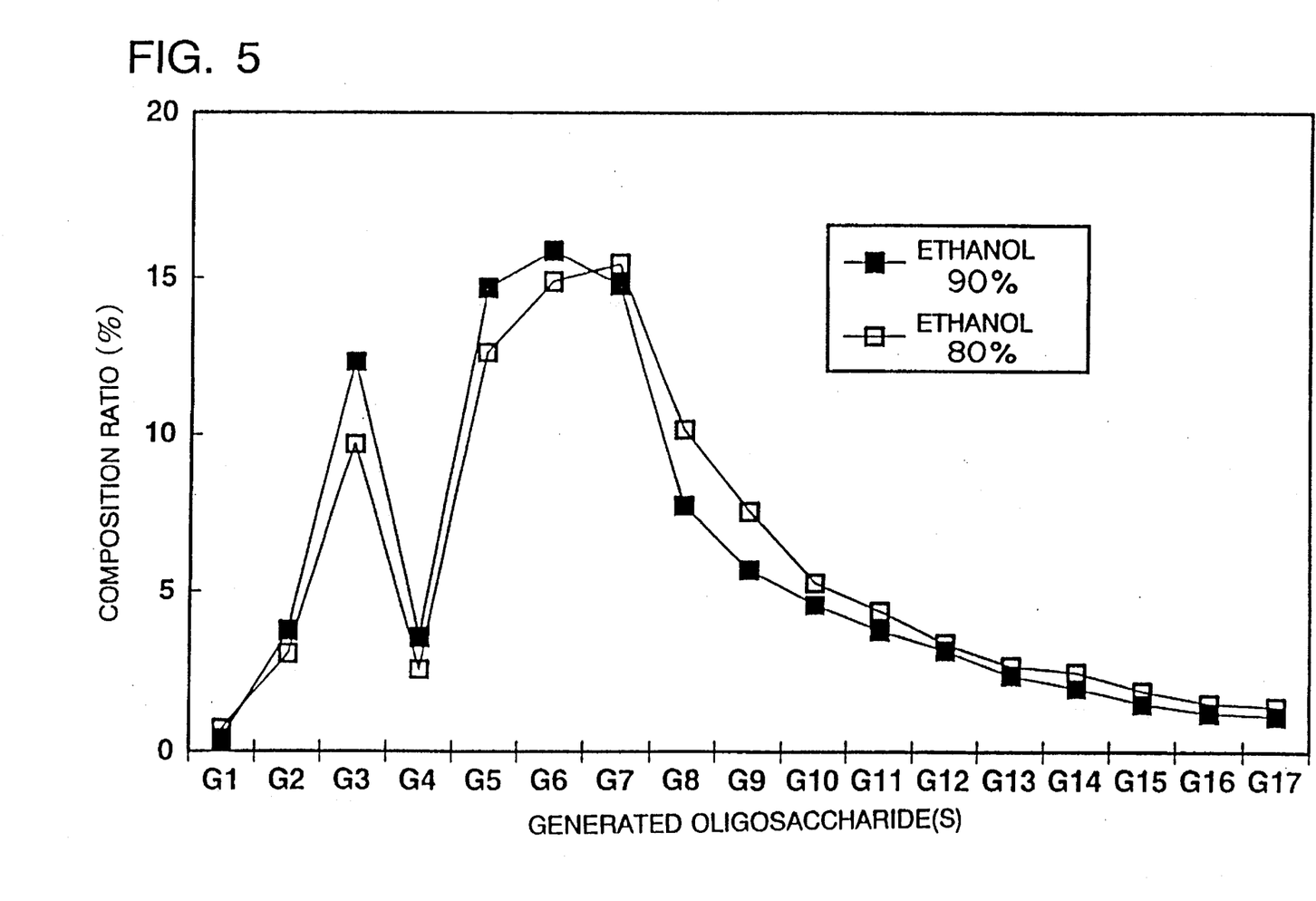
FIG. 5 is a set of graphs depicting the ratios of individual oligosaccharides of various polymerization degrees to the total amount of the reaction products.

The reaction was furthermore effected in a higher concentration of ethanol. Using as the enzyme 0.8 g of the immobilized Termamil 120L in 10 ml of the reaction solution, the reaction was effected as described above followed by the analysis of the precipitate. The reaction was effected for 190 hours in the reaction solution at pH 6.0. The results are shown in Table 5 and FIG. 5.

TABLE 5

| polymerization degree | ethanol concentration (V/V %) | |
| --- | --- | --- |
| | 80 | 90 |
| 1 | 0.7 | 3.8 |
| 2 | 3.1 | 12.4 |
| 3 | 9.7 | 3.6 |
| 4 | 2.6 | 14.7 |
| 5 | 12.7 | 15.8 |
| 6 | 14.9 | 14.8 |
| 7 | 15.4 | 7.7 |
| 8 | 10.2 | 5.7 |
| 9 | 7.5 | 4.6 |
| 10 | 5.3 | 3.8 |
| 11 | 4.4 | 3.2 |
| 12 | 3.4 | 2.4 |
| 13 | 2.7 | 2.0 |
| 14 | 2.5 | 1.5 |
| 15 | 1.9 | 1.2 |
| 16 | 1.5 | 1.1 |
| 17 | 1.4 | 0 |
| Yield (%) | 36.3 | 61.9 |

These results indicate that oligosaccharides of higher polymerization degrees which possibly might not be produced in water alone were generated even in ethanol of a higher concentration such as about 90%.

Example 6

Furthermore, by modifying the substrate concentration, the reaction products were analyzed.

Figure 6:
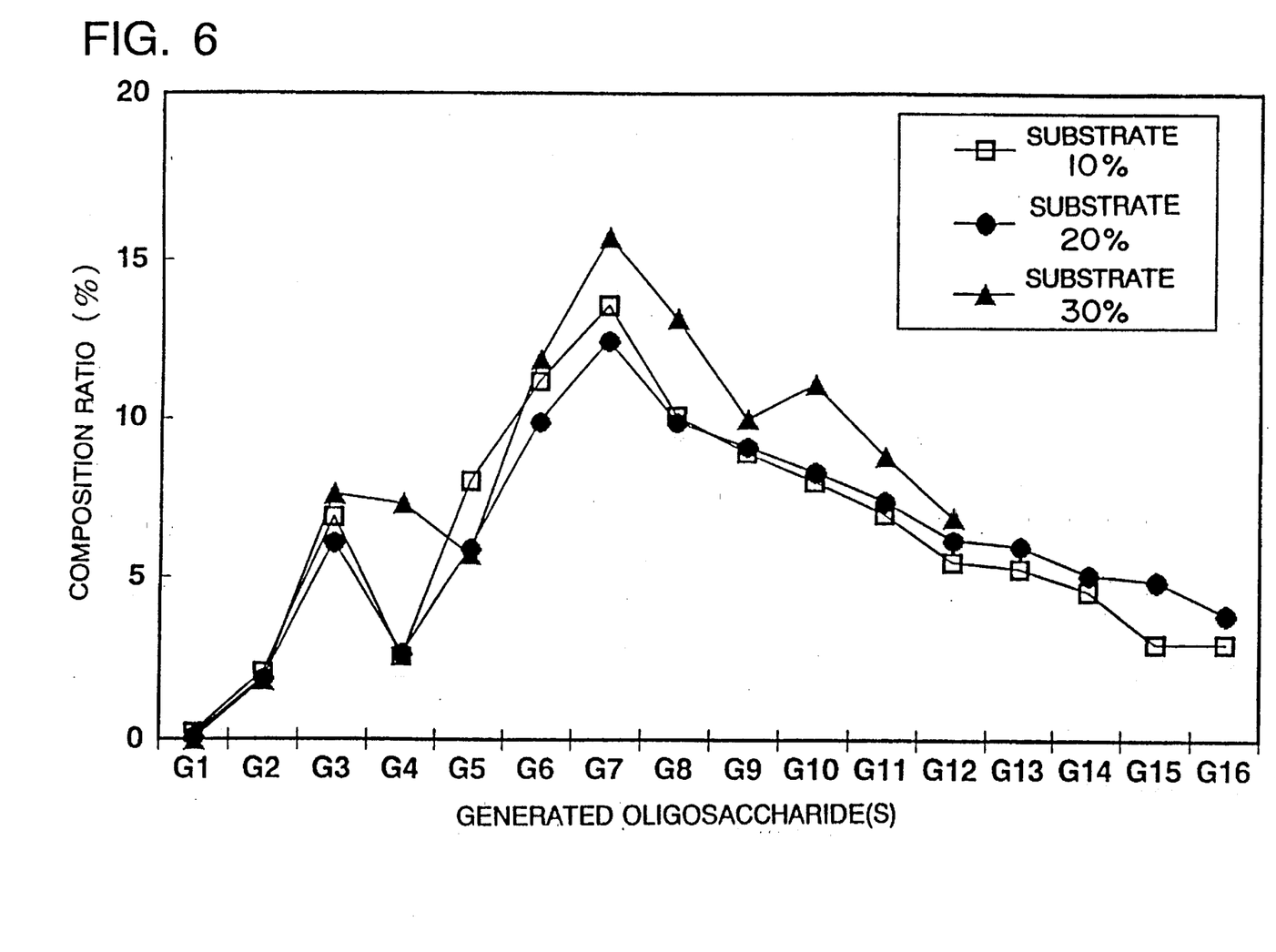
FIG. 6 is a set of graphs depicting the ratios of individual oligosaccharides of various polymerization degrees to the total amount of the reaction products.

As a substrate, wheat starch was suspended at 10, 20 and 30 w/v % in 90% ethanol (pH 6.0) for use; using 0.8 g of the immobilized Termamil 120L in 10 ml of the reaction solution, the reaction was effected at 50° C. for 24 hours. After the reaction, analysis was done about the products in the precipitate. The results are shown in Table 6 and FIG. 6.

TABLE 6

| polymerization degree | Substrate concentarion (%) | | |
| --- | --- | --- | --- |
| | 10 | 20 | 30 |
| 1 | 0.2 | 0.1 | — |
| 2 | 2.1 | 1.9 | 1.8 |
| 3 | 6.9 | 6.1 | 7.6 |
| 4 | 2.6 | 2.7 | 7.3 |
| 5 | 8.0 | 5.9 | 5.7 |
| 6 | 11.2 | 9.9 | 11.9 |
| 7 | 13.6 | 12.5 | 15.7 |
| 8 | 10.1 | 9.9 | 13.2 |
| 9 | 8.9 | 9.1 | 10.0 |
| 10 | 8.0 | 8.3 | 11.1 |
| 11 | 7.0 | 7.2 | 8.8 |
| 12 | 5.5 | 6.2 | 6.9 |
| 13 | 5.3 | 6.0 | 0 |
| 14 | 4.6 | 5.1 | 0 |
| 15 | 3.0 | 4.9 | 0 |
| 16 | 3.0 | 3.9 | 0 |
| Yield (%) | 18.5 | 9.8 | 1.8 |

These results indicate that the substrate concentration hardly has any influence on the ratios of oligosaccharides of higher polymerization degrees in the products, and that far higher concentrations of the substrate decrease the yield. As in the present Example, the concentration of the substrate starch is preferably 20 w/v % or less in terms of yield, when the ethanol concentration is higher.

Example 7

Furthermore, enzymatic degradation was effected changing the kind of substrate starch.

Figure 7:
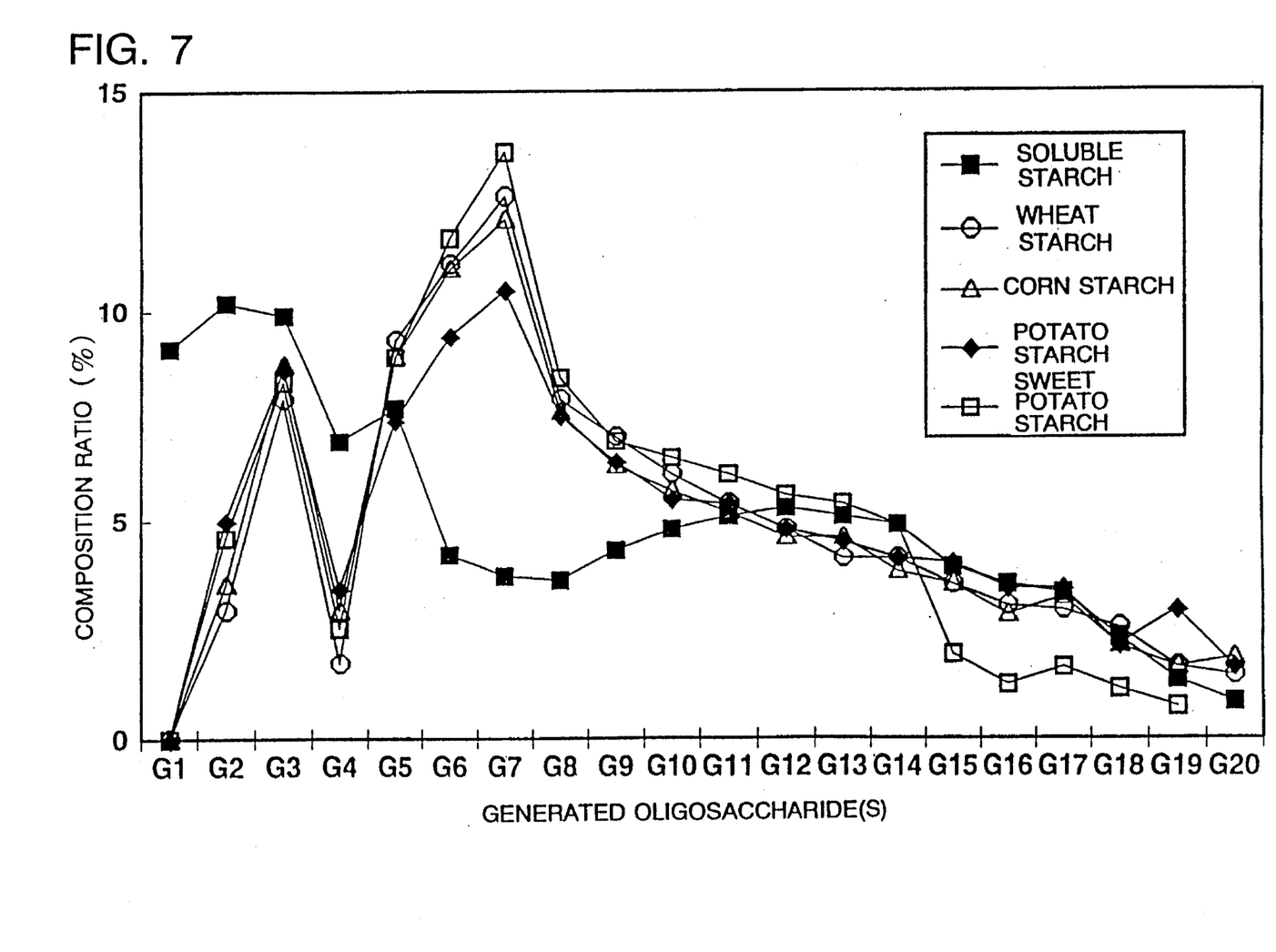
FIG. 7 is a set of graphs depicting the ratios of individual oligosaccharides of various polymerization degrees to the total amount of the reaction products.

Adding 0.8 g of the immobilized Termamil 120L in 10 ml each of 20 w/v % soluble starch, wheat starch, corn starch, potato starch, and sweet potato starch suspension in 90% ethanol, the reaction was effected at 50° C. for 240 hours. The products in the precipitates were analyzed, and the results are shown in Table 7 and FIG. 7.

TABLE 7

| polymerization degree | Kind of substrate starch | | | | |
| --- | --- | --- | --- | --- | --- |
| | Soluble | Wheat | Corn | Potato | Sweet Potato |
| 1 | 9.1 | 0 | 0 | 0 | 0 |
| 2 | 0.2 | 2.9 | 3.5 | 5.0 | 4.6 |
| 3 | 9.9 | 7.9 | 8.7 | 8.6 | 8.3 |
| 4 | 6.9 | 1.7 | 2.9 | 3.4 | 2.5 |
| 5 | 7.7 | 9.3 | 8.9 | 7.4 | 8.9 |
| 6 | 4.2 | 11.1 | 11.0 | 9.4 | 11.7 |
| 7 | 3.7 | 12.6 | 12.1 | 10.5 | 13.6 |
| 8 | 3.6 | 7.9 | 7.6 | 7.5 | 8.4 |
| 9 | 4.3 | 7.0 | 6.3 | 6.4 | 6.9 |
| 10 | 4.8 | 6.1 | 5.7 | 5.5 | 6.5 |
| 11 | 5.1 | 5.4 | 5.2 | 5.4 | 6.1 |
| 12 | 5.3 | 4.8 | 4.6 | 4.8 | 5.6 |
| 13 | 5.1 | 4.1 | 4.6 | 4.5 | 5.4 |
| 14 | 4.9 | 4.1 | 3.8 | 4.1 | 4.9 |
| 15 | 3.9 | 3.5 | 3.5 | 4.0 | 1.9 |
| 16 | 3.5 | 3.0 | 2.8 | 3.4 | 1.2 |
| 17 | 3.3 | 2.9 | 3.2 | 3.4 | 1.6 |
| 18 | 2.3 | 2.5 | 2.1 | 2.1 | 1.1 |
| 19 | 1.3 | 1.6 | 1.6 | 2.9 | 0.7 |
| 20 | 0.8 | 1.4 | 1.8 | 1.6 | 0 |

These results indicate that oligosaccharides of higher polymerization degrees were generated through ethanol addition to the reaction solutions with no relation to the kinds of starch.

Example 8

Explanation will now follow of the example where oligosaccharides of higher polymerization degree degrees were generated from starch in the presence of ethanol, using α-amylase in combination with pullulanase as hydrolases.

Figure 8:
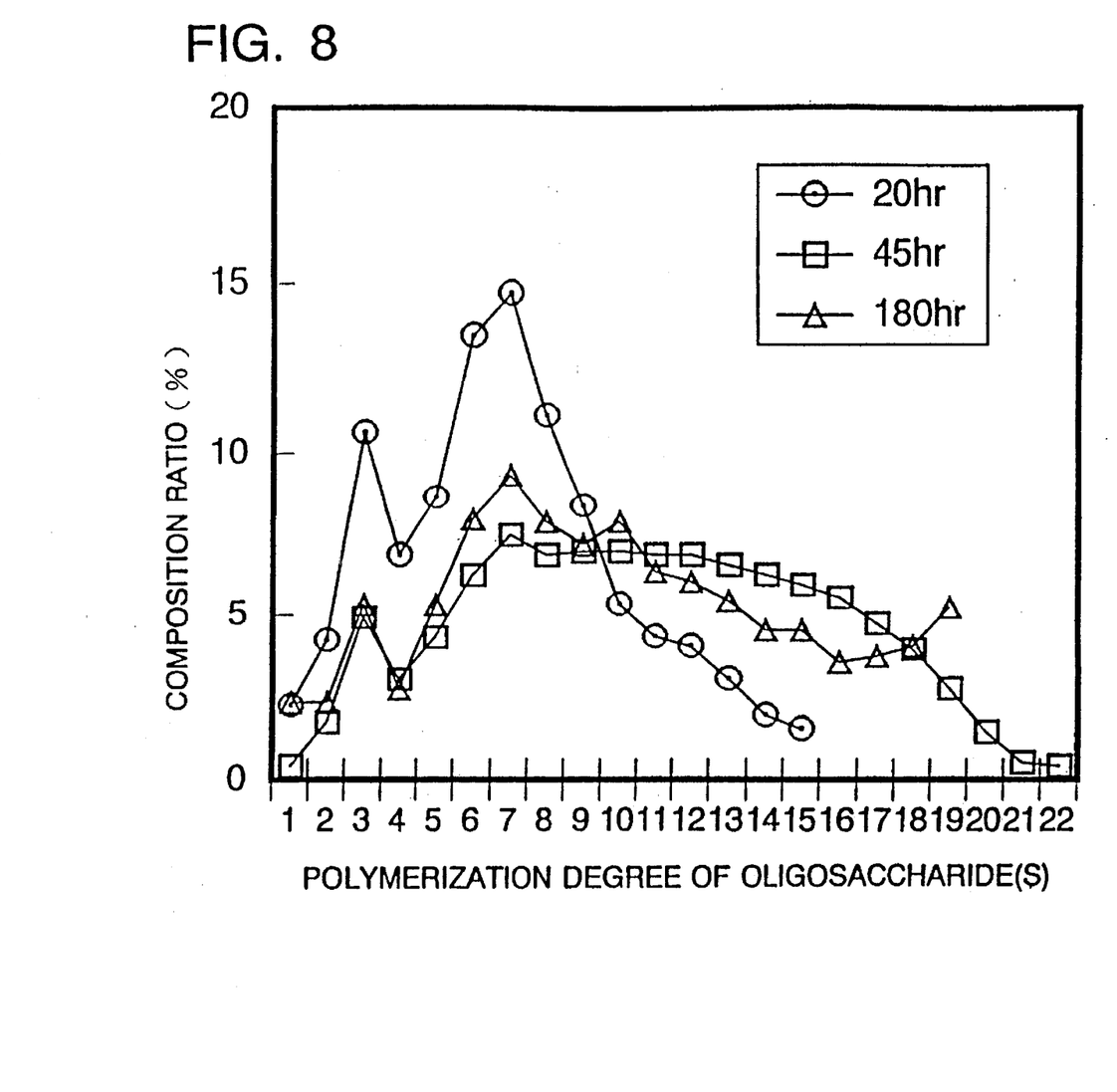
FIG. 8 is a set of graphs depicting the ratios of individual oligosaccharides of various polymerization degrees to the total amount of the reaction products.
Figure 9:
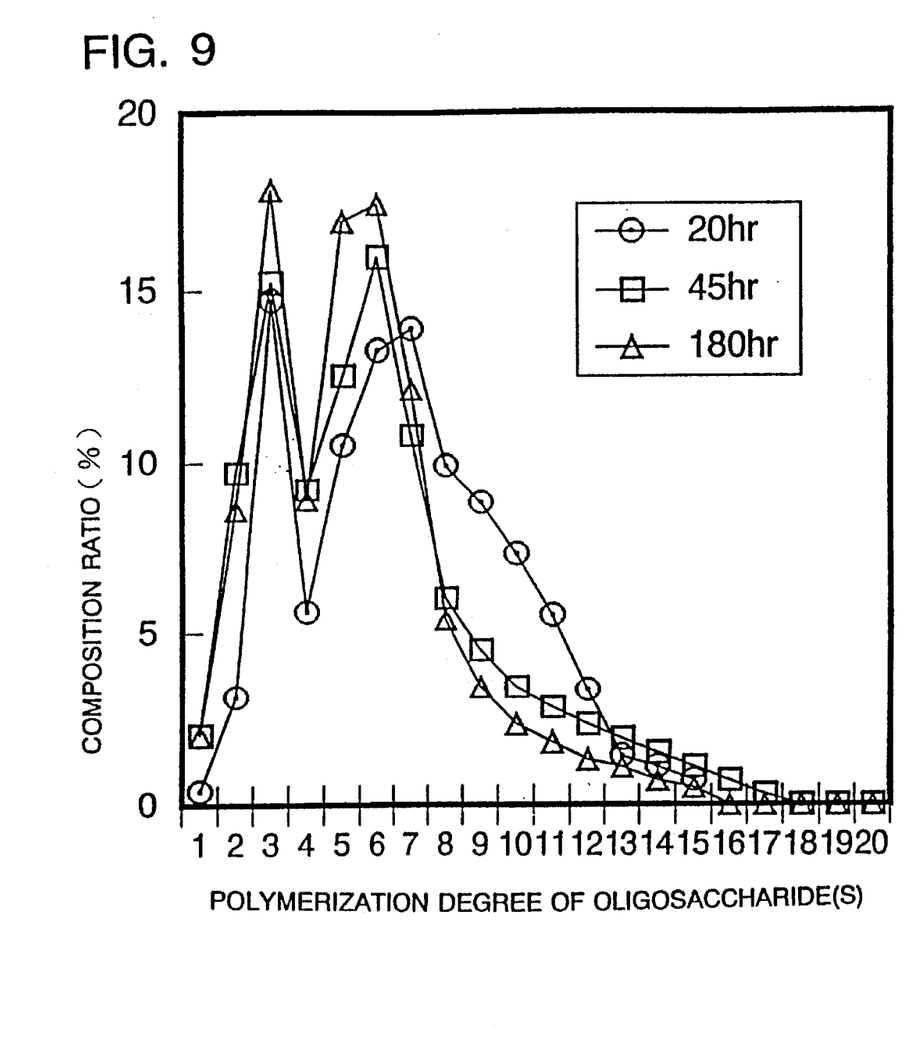
FIG. 9 is a set of graphs depicting the ratios of individual oligosaccharides of various polymerization degrees to the total amount of the reaction products.

Potato starch was suspended at 10 w/v % in 85 v/v % ethanol solution (pH 7.0), and the reaction was effected at 50 C. using 0.4 g each of the individually immobilized Termamil 120L and pullulanase "AMANO" (manufactured by AMANO Pharmaceuticals; derived from *Krebsiella pneumoniae*) in 10 ml of the reaction solutions. The concentrations of the oligosaccharides contained in the precipitates were determined, and the ratios of the individual oligosaccharides of various polymerization degrees to the total weights are shown in FIG. 8. The yield of the oligosaccharides (polymerization degrees of 20 or less; the same is true hereinbelow) after 180-hr reaction was 61.1%. Also, the reaction was effected when the concentration of potato starch in the reaction system was modified under the same conditions. The results are shown in FIG. 9. The yield after 180-hr reaction was 52.6% in case that the starch concentration was 20%; 66.5% in case that the starch concentration was 30%.

Figure 10:
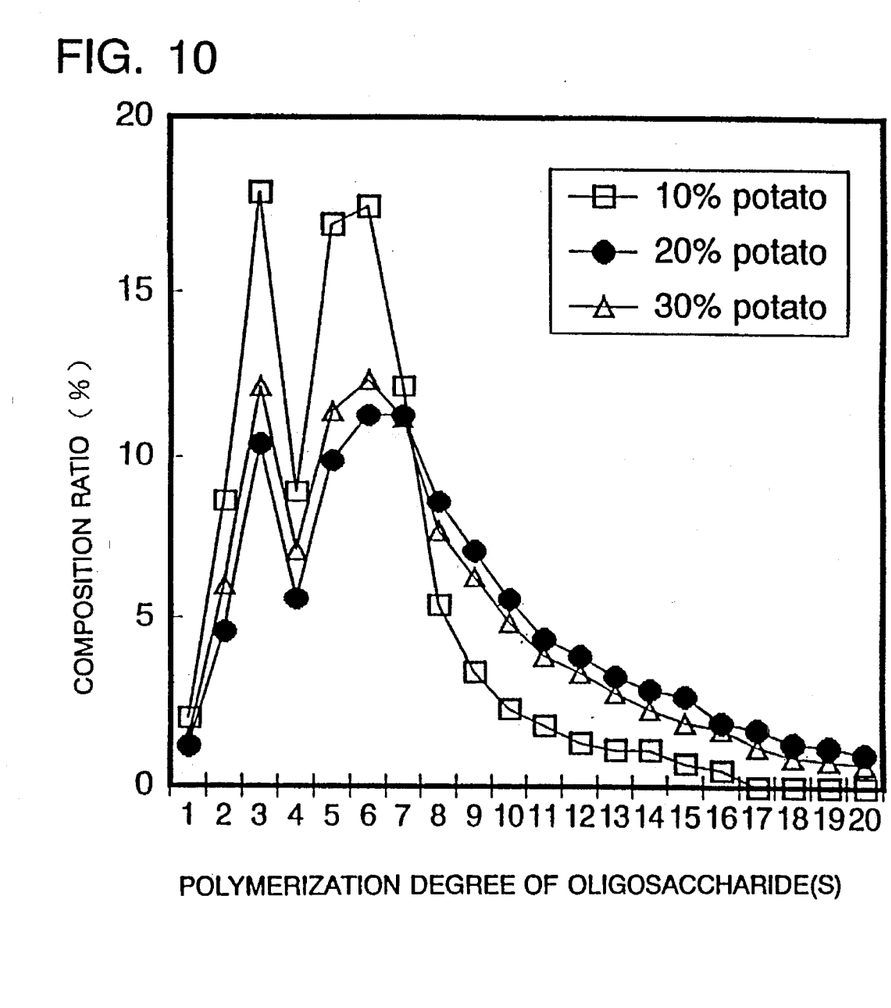
FIG. 10 is a set of graphs depicting the ratios of individual oligosaccharides of various polymerization degrees to the total amount of the reaction products.

Using 0.8 g of the immobilized Termamil 120L alone as hydrolase in 10 ml of the reaction solution, the reaction was effected as described above. The results are shown in FIG. 10. The yield after 180-hr reaction was 7.5%.

As shown in the Examples 2 and 3, the ratios of the oligosaccharides of higher polymerization degrees did increase as the ethanol concentration was elevated but the total yield was lowered, in case that α-amylase alone was used; alternatively, a higher yield was realized at a higher ethanol concentration when pullulanase was used in combination with α-amylase, which indicates that the polymerization degree and the yield both can be improved.

As shown in Example 6, furthermore, the yield was lowered at a higher ethanol concentration when the substrate concentration was higher, but the higher yield can be maintained when pullulanase is used together with amylase even at a higher substrate concentration such as 30%.

INDUSTRIAL APPLICABILITY

In accordance with the present invention, enzymatic degradation of a polysaccharide is carried out in a mixture system of a hydrophilic organic solvent and water, whereby oligosaccharides of higher polymerization degrees can be produced at a higher efficiency.

We claim:

1. A method of producing oligosaccharides in the size range from pentamer to 20-mer, said method consisting essentially of the steps of:

enzymatically hydrolysing a polysaccharide selected from the group consisting of starch, pullulan, and dextran using at least one hydrolase selected from the group consisting of α-amylase, pullulanase, and dextranase, in an amount and for a time sufficient to degrade the polysaccharide, in an aqueous solution of a hydrophilic organic solvent and water, said hydrophilic organic solvent being selected from the group consisting of methanol, ethanol and propanol and being at a concentration of 30% to 90% by volume in said aqueous solution, in which the distribution of polymerization degree values of oligosaccharides generated as a result of reaction of said at least one hydrolase on said polysaccharide is shifted to the range of from 5 to 20; and recovering the oligosaccharides having a polymerization degree of 5–20 from the reaction mixture.

2. A method according to claim 1, wherein said hydrophilic organic solvent is ethanol.

3. A method according to claim 1, wherein said polysaccharide comprises starch and said hydrolase consists essentially of amylase and pullulanase.

4. A method according to claim 3, wherein said amylase and pullulanase are contained in a ratio of 1:1.

5. A method according to claim 1, wherein the hydrophilic organic solvent is at a concentration of 60 to 90 v/v % in said aqueous solution.

6. A method according to claim 5, wherein the recovering step comprises centrifuging the reaction mixture to collect the resultant precipitated oligosaccharides in the size range from pentamer to 20-mer, and purifying the oligosaccharides.

* * * * *

UNITED STATES PATENT AND TRADEMARK OFFICE
CERTIFICATE OF CORRECTION

PATENT NO. : 5,580,762
DATED : December 3, 1996
INVENTOR(S) : Isao Karube and Takashi Morita It is certified that error appears in the above-indentified patent and that said Letters Patent is hereby corrected as shown below:

On the title page: Item [73] Assignee, add -- Akebono Research and Development Centre Ltd.-- as a second Assignee.

Signed and Sealed this

Seventeenth Day of June, 1997

*Attest:*

BRUCE LEHMAN

*Attesting Officer*     *Commissioner of Patents and Trademarks*